US011874199B2

United States Patent
Gosse et al.

(10) Patent No.: US 11,874,199 B2
(45) Date of Patent: Jan. 16, 2024

(54) DEVICE AND PROCESS FOR DETERMINING THE SIZE OF A LEAK HOLE IN A SAMPLE

(71) Applicant: ANEOLIA, Moissy-Cramayel (FR)

(72) Inventors: Thierry Gosse, Villebon-sur-Yvette (FR); Philippe Lacarrere, Nangis (FR); Eric Schaller, Varennes-Jarcy (FR)

(73) Assignee: ANEOLIA, Moissy-Cramayel (FR)

( * ) Notice: Subject to any disclaimer, the term of this patent is extended or adjusted under 35 U.S.C. 154(b) by 196 days.

(21) Appl. No.: 16/184,037

(22) Filed: Nov. 8, 2018

(65) Prior Publication Data

US 2019/0072453 A1 Mar. 7, 2019

Related U.S. Application Data

(62) Division of application No. 14/653,613, filed as application No. PCT/EP2013/077538 on Dec. 19, 2013, now Pat. No. 10,197,469.

(30) Foreign Application Priority Data

Dec. 21, 2012 (FR) ...................................... 1262680

(51) Int. Cl.
*G01M 3/32* (2006.01)
*G01N 33/00* (2006.01)
(Continued)

(52) U.S. Cl.
CPC ................. *G01M 3/32* (2013.01); *G01F 5/00* (2013.01); *G01F 9/00* (2013.01); *G01M 3/007* (2013.01);
(Continued)

(58) Field of Classification Search
CPC .......... G01M 3/32; G01M 3/007; G01N 7/10; G01N 33/0004; G01N 27/18; G01F 1/34; G01F 9/00; G01F 5/00
(Continued)

(56) References Cited

U.S. PATENT DOCUMENTS 3,818,752 A * 6/1974 Lindeberg ........... G01M 3/3254
73/49.2
3,852,996 A * 12/1974 Klaubert ................ G01M 3/26
73/40.5 R
(Continued)

FOREIGN PATENT DOCUMENTS

| CN | 102057153 A * | 5/2011 | ......... F02M 25/0809 |
| EP | 1923312 | 5/2008 | |
| WO | 2008/046420 | 4/2008 | |

OTHER PUBLICATIONS

Steckelmacher et al., "Thermal Conductivity Leak Detectors Suitable for Testing Equipment by Overpressure or Vacuum", Vacuum (1962), 12(3), pp. 153-159.
(Continued)

*Primary Examiner* — Peter J Macchiarolo
*Assistant Examiner* — Monica S Young
(74) *Attorney, Agent, or Firm* — Greer, Burns & Crain, Ltd

(57) ABSTRACT

A device for testing a sample via a gas stream that includes an opening, a generator for generating a gas stream in the device along at least one flow path, at least one pressure sensor, and a mass flowmeter configured to measure the mass flow rate of the gas stream along each flow path. The flow path including an exhaust path terminating at the opening, and the gas stream generator configured to exhaust a leakage gas along the exhaust path. The pressure sensor includes an exhaust pressure sensor configured to measure a pressure of the leakage gas along the exhaust path, and the
(Continued)

mass flowmeter is configured to measure a parameter representing the mass flow rate of the leakage gas along the exhaust path. A calculation device determines the size of a leak hole, based on a measurement of the parameter representing the mass flow rate along the exhaust path.

22 Claims, 4 Drawing Sheets

(51) Int. Cl.
    *G01N 7/10* (2006.01)
    *G01N 27/18* (2006.01)
    *G01F 5/00* (2006.01)
    *G01F 9/00* (2006.01)
    *G01F 1/34* (2006.01)
    *G01M 3/00* (2006.01)

(52) U.S. Cl.
    CPC .......... G01N 7/10 (2013.01); G01N 33/0004 (2013.01); G01N 27/18 (2013.01)

(58) Field of Classification Search
    USPC .......................................................... 73/37
    See application file for complete search history.

(56) References Cited

U.S. PATENT DOCUMENTS

| | | | | |
|---|---|---|---|---|
| 4,685,331 A * | 8/1987 | Renken | ................. | G01F 1/6842 137/486 |
| 4,776,206 A * | 10/1988 | Armstrong | .......... | G01M 3/3254 73/40 |
| 4,787,254 A * | 11/1988 | Duckworth | ............... | G01F 1/36 73/861.62 |
| 4,896,528 A * | 1/1990 | Lewis | ..................... | G01M 3/02 73/40.7 |
| 4,898,021 A * | 2/1990 | Weaver | ................. | G01M 3/202 73/40.7 |
| 5,369,984 A * | 12/1994 | Rogers | ................ | G01M 3/3263 73/49.2 |
| 5,513,516 A * | 5/1996 | Stauffer | .............. | G01M 3/3218 73/49.2 |
| 5,861,547 A * | 1/1999 | Kawai | ................... | G01M 3/227 73/49.2 |
| 6,308,556 B1 * | 10/2001 | Sagi | ..................... | G01M 3/3254 73/40 |
| 6,382,011 B1 * | 5/2002 | Mayer | ................. | G01F 25/0007 73/1.06 |
| 9,784,639 B2 * | 10/2017 | Wetzig | ................ | G01M 3/3281 |
| 10,900,862 B2 * | 1/2021 | Decker | .................. | G01M 3/04 |
| 2001/0003917 A1 * | 6/2001 | Sagi | ........................ | G01M 3/04 73/40 |
| 2003/0015021 A1 * | 1/2003 | Mayer | .................. | G01M 3/227 73/40.7 |
| 2003/0019286 A1 * | 1/2003 | Wakahara | .......... | F02M 25/0809 73/114.41 |
| 2003/0046983 A1 * | 3/2003 | Sato | ......................... | G01N 7/00 73/53.01 |
| 2003/0192370 A1 * | 10/2003 | Amano | .............. | F02M 25/0809 73/114.41 |
| 2005/0072221 A1 * | 4/2005 | Itakura | ................... | F02M 25/08 73/114.41 |
| 2005/0252770 A1 | 11/2005 | Naito et al. | | |
| 2007/0039466 A1 | 2/2007 | Nawata et al. | | |
| 2007/0044549 A1 * | 3/2007 | Yoshioka | .......... | F02M 25/0809 73/114.39 |
| 2007/0199374 A1 * | 8/2007 | Shibuya | .............. | F02D 41/0045 73/114.39 |
| 2007/0246025 A1 * | 10/2007 | Sato | .................... | F02M 25/0827 123/520 |
| 2007/0266773 A1 * | 11/2007 | Mayer | ................. | G01M 3/3272 73/49.3 |
| 2008/0092635 A1 * | 4/2008 | Mayer | .................. | G01M 3/226 73/49.3 |
| 2008/0163677 A1 * | 7/2008 | Mayer | ................. | G01M 3/3272 73/49.3 |
| 2009/0038409 A1 | 2/2009 | Ruchel | | |
| 2009/0165534 A1 * | 7/2009 | Kohno | ................ | G01M 3/2815 73/49.1 |
| 2010/0089146 A1 | 4/2010 | Morita et al. | | |
| 2010/0313634 A1 * | 12/2010 | Wetzig | ..................... | G01M 3/20 73/40.7 |
| 2011/0231136 A1 * | 9/2011 | Tindall | ................... | G01N 13/00 702/100 |
| 2011/0303019 A1 * | 12/2011 | Gysling | ................. | G01F 1/712 73/861.07 |
| 2013/0041234 A1 | 2/2013 | Grinstein et al. | | |
| 2013/0325194 A1 * | 12/2013 | Brine | ................... | G05D 7/0629 700/282 |
| 2014/0311222 A1 * | 10/2014 | Decker | .................. | G01M 3/02 73/40 |
| 2014/0356523 A1 * | 12/2014 | Fultz | ................... | H01M 50/193 427/58 |
| 2015/0226629 A1 | 8/2015 | Murthy | | |
| 2018/0328812 A1 * | 11/2018 | Fukushima | ......... | G01M 3/3272 |

OTHER PUBLICATIONS

European Search Report from European Patent Application No. 18170505.4, dated Jun. 11, 2018.
W.M. Sears et al, "Surface Adsorption and Gas Consumption in Restricted Flow, Thermally Driven, Gas Sensors", Semicond. Sci. Tehcnol., No. 5, 1990, pp. 45-53.
Witt-Gasetechnik Gmbh & Co KG, "Instruction Manual Oxybaby M+ 02/CO2", Aug. 23, 2010.

* cited by examiner

DEVICE AND PROCESS FOR DETERMINING THE SIZE OF A LEAK HOLE IN A SAMPLE

CROSS-REFERENCE TO RELATED APPLICATIONS

This application is a divisional of and claims priority to U.S. patent application Ser. No. 14/653,613 filed on Jun. 18, 2015, the entire contents of which is incorporated herein by reference.

BACKGROUND

The present invention relates to a device for testing a sample. It also relates to a process implemented by this device.

Such a device allows a user to test a sample, for example to cause dynamic stress to be generated in the sample by dynamically reversible flow, and/or to measure the integrity of the envelope of the sample, and/or to measure the breathability of the sample, and/or to differentiate a gas within this sample, etc.

Systems for testing samples are known, for example for measuring the proportion of a given gas within the sample or for measuring a leak or a problem relating to tightness of the sample.

A recurrent drawback of the solutions of the state of the art is that they are too costly, take too long (typical response time of some twelve seconds for an infra-red measurement of $CO_2$ proportion), or are insufficiently accurate (minimum measurable size of a leak hole of 5 μm with a relative excess pressure of 500 mbar, or with helium flushing in the enclosure being measured).

The purpose of the present invention is to propose a device and a process for testing a sample having at least one of the following technical advantages:
- low production cost with respect to the state of the art,
- high measurement speed with respect to the state of the art, and
- high measurement resolution with respect to the state of the art.

SUMMARY

This objective is achieved with a device for testing a sample via a gas stream, comprising:
- an opening,
- means for generating a gas stream in the device along at least one flow path passing through the opening,
- at least one pressure sensor, each pressure sensor being arranged in order to measure a pressure of the gas stream along at least one flow path, and
- a mass flowmeter, arranged in order to measure a parameter representing the mass flow rate of the gas stream along each flow path.

According to a first aspect of the device according to the invention:
- the at least one flow path can comprise a suction path starting at the opening,
- the means for generating the gas stream can be arranged in order to suck in a gas to be analyzed so that this gas to be analyzed flows along the suction path,
- within the device, said suction path can narrow locally at a measurement hole,
- the at least one pressure sensor can comprise a suction pressure sensor arranged in order to measure a pressure of the gas to be analyzed along the suction path,
- the mass flowmeter can be arranged in order to measure a parameter representing the mass flow rate of the gas to be analyzed along the suction path, and
- the device can also comprise calculation means arranged in order to quantify the presence of a gas of interest within the gas to be analyzed, based on a measurement of the parameter representing the mass flow rate of the gas to be analyzed along the suction path.

The mass flowmeter is preferably a mass flowmeter using thermal conductivity.

The calculation means can be arranged in order to quantify the presence of the gas of interest in the form of a calculation of a proportion of the gas of interest which depends on the diameter of the measurement hole.

The suction pressure sensor can be situated along the suction path between the opening and the measurement hole.

The mass flowmeter can be situated along the suction path so that the measurement hole is situated along the suction path between the opening and the mass flowmeter.

The calculation means can be arranged in order to quantify the presence of the gas of interest in the form of a calculation of a proportion of the gas of interest which depends:
- affinely on the square root of the parameter representing the mass flow rate along the suction path, or
- affinely on the parameter representing the mass flow rate along the suction path.

The calculation means can be arranged in order to quantify the presence of the gas of interest also based on a measurement of the pressure along the suction path by the suction pressure sensor. The calculation means can be arranged in order to quantify the presence of the gas of interest in the form of a calculation of a proportion of the gas of interest which depends:
- affinely on the inverse of the fourth root of the measurement of the pressure along the suction path by the suction pressure sensor: the calculation means can be arranged in order to quantify the presence of the gas of interest in the form of a calculation of a proportion of the gas of interest according to the formula $$A\frac{\sqrt[2]{D_m}}{\sqrt[4]{P_r}} + B$$

with $D_m$ the parameter representing the mass flow rate, $P_r$ the pressure measured by the suction pressure sensor, and A and B being numerical calibration coefficients; or
- affinely on the inverse of the measurement of the pressure along the suction path by the suction pressure sensor. The calculation means can be arranged in order to quantify the presence of the gas of interest in the form of a calculation of a proportion of the gas of interest according to the formula:

$$M\frac{D_m}{P_r} + N$$

with $D_m$ the parameter representing the mass flow rate, $P_r$ the pressure measured by the suction pressure sensor, M and N being numerical calibration coefficients.

The calculation means can be arranged in order to trigger a quantification of the presence of the gas of interest for a value of the pressure along the suction path measured by the suction pressure sensor corresponding to a suction pressure reference value, the calculation means being then arranged in order to quantify the presence of the gas of interest based on a value of the parameter representing the mass flow rate along the suction path measured simultaneously with the pressure measurement measuring the pressure value corresponding to the suction pressure reference value. The calculation means can be arranged in order to quantify the presence of the gas of interest in the form of a calculation of a proportion of the gas of interest according to the formula:

$$A^* \sqrt[2]{D_m} + B$$

with $D_m$ the parameter representing the mass flow rate, and $A^*$ and B being numerical calibration coefficients, or $M^*D_m+N$ with $D_m$ the parameter representing the mass flow rate, and $M^*$ and N being numerical calibration coefficients.

The calculation means can also be arranged in order to quantify the presence of a first molecule of interest of the gas of interest having a certain thermal conductivity, the device also comprising along the suction path at least one gas sensor arranged in order to quantify the presence of at least one other molecule of interest of the gas of interest which preferably has a thermal conductivity differing by at most 10% (preferably at most 5%) with respect to the thermal conductivity of the first molecule of interest under identical conditions, the calculation means being arranged in order to quantify the presence of the first molecule of interest based on a quantification of the presence of the gas of interest and a quantification of the presence of the other molecules of interest.

The at least one flow path can comprise a dilution path terminating at the opening, the means for generating the gas stream being then arranged in order to exhaust a dilution gas along the dilution path.

According to a second aspect of a device according to the invention that can be combined with the first aspect of a device according to the invention:
- the at least one flow path can comprise an exhaust path terminating at the opening,
- the means for generating the gas stream can be arranged in order to exhaust a leakage gas along the exhaust path,
- the at least one pressure sensor can comprise an exhaust pressure sensor arranged in order to measure a pressure of the leakage gas along the exhaust path,
- the mass flowmeter can be arranged in order to measure a parameter representing the mass flow rate of the leakage gas along the exhaust path, and
- the device can also comprise calculation means arranged in order to determine the size of a leak hole of a sample connected to the opening, based on a measurement of the parameter representing the mass flow rate along the exhaust path.

The mass flowmeter is preferably a mass flowmeter using thermal conductivity.

The exhaust pressure sensor is preferably situated along the exhaust path between the flowmeter and the opening.

The calculation means can be arranged in order to determine the size of the leak hole in the form of a calculation which depends affinely on the square root of the parameter representing the mass flow rate along the exhaust path.

The calculation means can be arranged in order to determine the size of the leak hole also based on a measurement of the pressure along the exhaust path by the exhaust pressure sensor. The calculation means can be arranged in order to determine the size of the leak hole in the form of a calculation which depends affinely on the inverse of the fourth root of the measurement of the pressure along the exhaust path. The calculation means can be arranged in order to determine the size of the leak hole according to the formula $$a \frac{\sqrt[2]{D_m}}{\sqrt[4]{P_r}} + b$$

with $D_m$ the parameter representing the mass flow rate, $P_r$ the pressure measured by the exhaust pressure sensor, and a and b being numerical calibration coefficients.

The calculation means can be arranged in order to trigger a determination of the size of the leak hole for a value of the pressure along the exhaust path measured by the exhaust pressure sensor corresponding to an exhaust pressure reference value, the calculation means being arranged in order to determine the size of the leak hole based on a value of the parameter representing the mass flow rate along the exhaust path measured simultaneously with the pressure measurement measuring the pressure value corresponding to the exhaust pressure reference value. The calculation means can be arranged in order to determine the size of the leak hole according to the formula $$a^* \sqrt[2]{D_m} + b$$

with $D_m$ the parameter representing the mass flow rate, and $a^*$ and b being numerical calibration coefficients.

The at least one flow path can comprise a calibration path passing through the opening, and within the device, said calibration path can narrow locally at a measurement hole, the calculation means being preferably arranged in order to:
- determine the size of the measurement hole based on a measurement of the parameter representing the mass flow rate along the calibration path, and
- adjust calibration coefficients for the calculation of a size of a leak hole if the determination of the size of the measurement hole does not correspond to an actual size of the measurement hole stored by the calculation means.

The device according to the invention can comprise a valve arranged to complete the exhaust path via a short-circuit path passing through the opening and the stream generation means but not passing through the flowmeter, said valve being preferably arranged in order to adjust the total flow rate passing through the exhaust path and the short-circuit path.

A process is also proposed for testing a sample via a gas stream, preferably implemented in the first aspect of the device according to the invention, and characterized in that it comprises:
- sucking a gas to be analyzed originating from a sample, said sucked gas to be analyzed flowing along a suction path starting by an opening linked to the sample, said suction path narrowing locally at a measurement hole, a pressure measurement of the gas to be analyzed along the suction path, a measurement of a parameter representing the mass flow rate of the gas to be analyzed along the suction path, and a quantification of the presence of a gas of interest within the gas to be analyzed, based on the measurement of the parameter representing the mass flow rate along the suction path.

The measurement of a parameter representing the mass flow rate is preferably a measurement by a mass flowmeter using thermal conductivity.

The quantification of the presence of the gas of interest can comprise a calculation of a proportion of the gas of interest which depends on the diameter of the measurement hole.

The pressure measurement can be carried out by a suction pressure sensor situated along the suction path between the sample and the measurement hole.

The measurement of the parameter representing the mass flow rate can be carried out by a mass flowmeter situated along the suction path so that the measurement hole is situated along the suction path between the sample and the mass flowmeter.

The quantification of the presence of the gas of interest can comprise a calculation of a proportion of the gas of interest which depends affinely on the square root of the parameter representing the mass flow rate along the suction path.

The quantification of the presence of the gas of interest can comprise a calculation of a proportion of the gas of interest which depends affinely on the parameter representing the mass flow rate along the suction path.

The quantification of the presence of a gas of interest can be carried out also based on the pressure measured along the suction path. The quantification of the presence of the gas of interest can comprise a calculation of a proportion of the gas of interest which depends affinely on:

the inverse of the fourth root of the measurement of the pressure along the suction path. The quantification of the presence of the gas of interest can comprise a calculation of a proportion of the gas of interest according to the formula $$A \frac{\sqrt[2]{D_m}}{\sqrt[4]{P_r}} + B$$

with $D_m$ the parameter representing the mass flow rate, $P_r$ the pressure measured, and A and B being numerical calibration coefficients; or the inverse of $P_r$ the pressure measured along the suction path. The quantification of the presence of the gas of interest can comprise a calculation of a proportion of the gas of interest according to the formula $$M \frac{D_m}{P_r} + N$$

with $D_m$ the parameter representing the mass flow rate, $P_r$ the pressure measured, M and N being numerical calibration coefficients.

The quantification of the presence of a gas of interest can be triggered in the case of a value of the pressure measured along the suction path corresponding to a suction pressure reference value, the quantification of the presence of a gas of interest being carried out based on a value of the parameter representing the mass flow rate along the suction path measured simultaneously with the pressure measurement measuring the pressure value corresponding to the pressure reference value. The quantification of the presence of the gas of interest can comprise a calculation of a proportion of the gas of interest according to the formula:

$$A^* \sqrt[2]{D_m} + B$$

with $D_m$ the parameter representing the mass flow rate, and A* and B being numerical calibration coefficients; or M* $D_m$+N with $D_m$ the parameter representing the mass flow rate, and M* and N being numerical calibration coefficients.

The gas of interest can comprise:
from 0 to 100% of a first molecule of interest having a certain thermal conductivity, and
from 0 to 100% of at least one other molecule of interest which has a thermal conductivity ideally differing by at most 10% (preferably at most 5%) with respect to the thermal conductivity of the first molecule of interest under identical conditions, and the process according to the invention can also comprise:
a quantification of the presence of the other molecules of interest within the gas to be analyzed by means of at least one gas sensor situated along the suction path, and
a quantification of the presence of the first molecule of interest in the gas to be analyzed based on the quantification of the presence of the gas of interest and the quantification of the presence of the other molecules of interest.

The at least one flow path can comprise a dilution path terminating at the opening, and the process according to the invention can comprise, before sucking the gas to be analyzed, exhausting a dilution gas flowing along the dilution path into the sample.

A process is also proposed for testing a sample via a gas stream, preferably implemented in the second aspect of device according to the invention, and comprising:
exhausting a leakage gas flowing along an exhaust path terminating in an opening linked to a sample,
measuring the pressure of the leakage gas along the exhaust path,
measuring a parameter representing the mass flow rate of the leakage gas along the exhaust path, and
determining the size of a leak hole in the sample, based on the measurement of the parameter representing the mass flow rate along the exhaust path.

The measurement of a parameter representing the mass flow rate is preferably a measurement by a mass flowmeter using thermal conductivity.

The pressure measurement can be carried out by an exhaust pressure sensor situated along the exhaust path between the flowmeter and the sample.

The determination of the size of the leak hole can comprise a calculation of the size of the leak hole which depends affinely on the square root of the parameter representing the mass flow rate along the exhaust path.

The determination of the size of the leak hole can be carried out also based on the pressure measured along the exhaust path. The determination of the size of the leak hole can comprise a calculation of the size of the leak hole which depends affinely on the inverse of the fourth root of the measurement of the pressure along the exhaust path. The determination of the size of the leak hole can comprise a calculation of the size of the leak hole according to the formula $$a \frac{\sqrt[2]{D_m}}{\sqrt[4]{P_r}} + b$$

with $D_m$ the parameter representing the mass flow rate, $P_r$ the pressure measured, and a and b being numerical calibration coefficients.

The determination of the size of the leak hole can be triggered in the case of a measured value of the pressure along the exhaust path corresponding to a pressure reference value, the determination of the size of the leak hole being carried out based on a value of the parameter representing the mass flow rate along the exhaust path measured simultaneously with the pressure measurement measuring the pressure value corresponding to the pressure reference value. The determination of the size of the leak hole can comprise a calculation of the size of the leak hole according to the formula $$a^* \sqrt[2]{D_m} + b$$

with $D_m$ the parameter representing the mass flow rate, and a* and b being numerical calibration coefficients.

The at least one flow path can comprise a calibration path passing through the opening and narrowing locally at a measurement hole, and the process according to the invention can comprise:
  a calibration gas flowing along the calibration path,
  a pressure measurement of the calibration gas along the calibration path,
  a measurement of a parameter representing the mass flow rate of the calibration gas along the calibration path,
  a determination of the size of the measurement hole based on a measurement of the parameter representing the mass flow rate, and
  an adjustment of numerical coefficients for the calculation of a size of a leak hole if the determination of the size of the measurement hole does not correspond to an actual size of the measurement hole stored by calculation means.

The process according to the invention can comprise an adjustment, by a valve arranged in order to complete the exhaust path via a short-circuit path passing through the opening and the stream generation means but not passing through the flowmeter, of the total flow rate passing through the exhaust path and the short-circuit path.

BRIEF DESCRIPTION OF THE DRAWINGS

Other advantages and features of the invention will become apparent on reading the detailed description of implementations and embodiments that are in no way limitative, and the attached drawings, in which.

DETAILED DESCRIPTION

Figure 1:
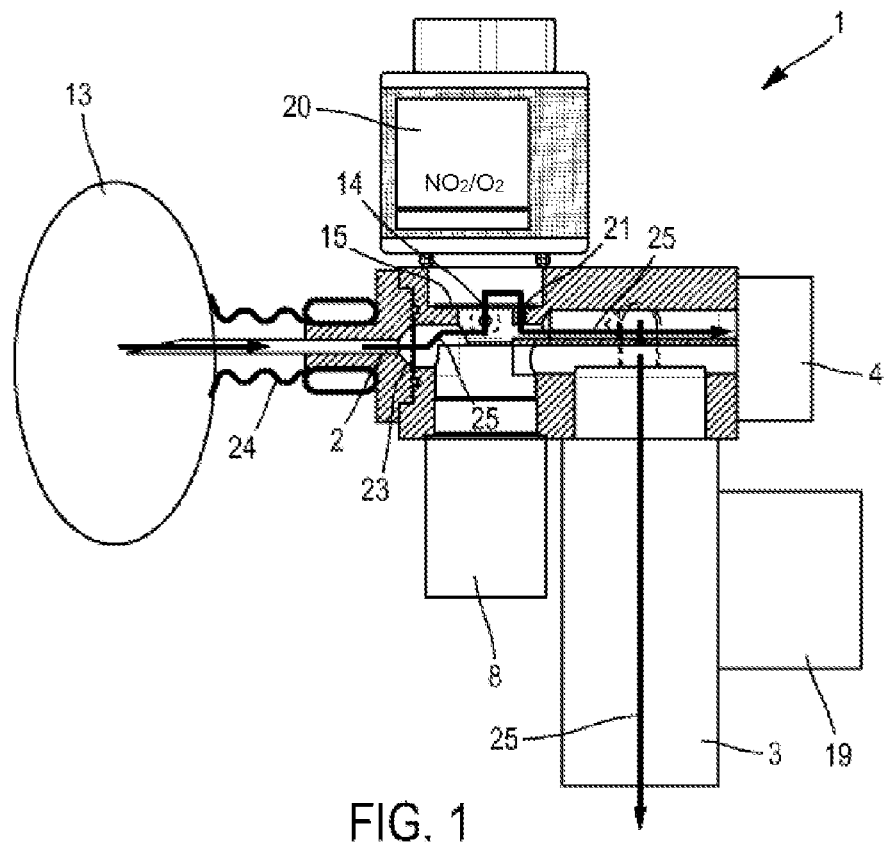
FIG. 1 is a diagrammatic cross section profile view of a device according to the invention, which is the preferred embodiment of the invention, and which shows a gas stream when this device is in a position for analysing a gas by suction or in a calibration position.

As these embodiments are in no way limitative, it is possible in particular to consider variants of the invention comprising only a selection of characteristics described below, in isolation from the other characteristics described (even if this selection is isolated within a sentence containing other characteristics), if this selection of characteristics is sufficient to confer a technical advantage or to differentiate the invention with respect to the prior art. This selection comprises at least one, preferably functional, characteristic without structural details, or with only a part of the structural details if this part alone is sufficient to provide a technical advantage or to distinguish the invention with respect to the prior art.

Firstly, a preferred embodiment of device 1 according to the invention will be described with reference to FIGS. 1 to 8. The device 1 is a compact technical sub-assembly capable of being installed in a portable system or incorporated within a fixed installation.

The device 1 is a device for testing a sample via a gas stream.

The device 1 comprises an opening 2. This opening 2 is the inlet opening of the hollow of a hollow needle, arranged at the centre of a gastight suction cup 24 arranged in order to be firmly placed against a sample 13 (such as a sachet of a food product or any container having at least one flexible surface of compatible dimensions capable of being passed through by a needle). The suction cup avoids the use of sealing septums in order to carry out a test without polluting the air outside the container.

The device 1 also comprises means 3 for generating a gas stream 25 (gas to be analyzed, dilution gas, leakage gas, calibration gas) in the device 1 along at least one flow path passing through the opening 2, via a mass flowmeter 4, and via a valve 8 called selection valve.

The valve 8 is a valve having more than two ways (inlet or outlet), having several possible positions. Each position of the valve 8 corresponds to a specific opening configuration for the passage of the gas stream 25 or closing configuration for preventing such passage between certain inlet and outlet ways of the valve 8.

The valve 8 is preferably a proportional valve (preferably drawer type).

The valve 8 is for example a valve produced based on a Mecalectro electromagnet or on a Parker valve.

The opening 2 and the valve 8 are common to all the flow paths. A microporous filter element 23 is preferably situated along this common part of the flow paths.

The filter 23 is for example a PTFE filter from Millipore or Sartorius.

The generation means 3 comprise a turbine, or more generally a reversible flow generator with speed control so as to have a controlled flow rate or pressure, for example made by Papst.

The generation means 3 are reversible, i.e. they are arranged in order to generate equally well a suction or exhaust (i.e. in a direction of flow opposite to the suction) gas stream 25.

A valve 16 and the opening 2 delimit the two ends of each of the flow paths.

The valve 16 is a valve having more than two ways (inlet or outlet), having several possible positions. According to the position of the valve 16, the valve 16 links the generation means 3 to the external atmosphere of the device 1 in a first position 17 or to a reference gas source 19 in a second position 18. The valve 16 is for example a valve made by Bosch or Univer.

The device 1 comprises at least one pressure sensor 5, 6, each pressure sensor 5, 6 being arranged in order to measure a pressure $P_r$ of the gas stream 25 along at least one of the flow paths. More precisely, the pressure Pr measured by each sensor 5 or 6 is a relative pressure (respectively under- or overpressure) generated by the stream 25 (sucked into the device 1 or exhausted from the device 1 respectively) with respect to the absolute pressure which would be measured in the absence of this stream 25. Each sensor 5, 6 is for example a piezoresistive sensor made by Honeywell, Freescale, or Sensortechnics.

The mass flowmeter 4 is arranged in order to measure a parameter representing the mass flow rate of the gas stream along each flow path. This parameter is typically an electrical intensity or an electrical voltage, and is preferably proportional to the mass flow rate of the gas stream 25 or linked to the mass flow rate of the gas stream 25 by a calculation that is programmed and/or stored within calculation means 7 of the device. All the sensor and control elements 5, 8, 6, 20, 4, 3, 16 are linked to the calculation means 7 by an electrical and/or data transfer or control connection (links shown in dotted lines in FIG. 2). The calculation and control means 7 are shown diagrammatically only in FIG. 2, to avoid overloading the other figures.

In the present document, the word "each" is used to denote any unit (for example a sensor or flow path) taken individually in an assembly. In the case where this assembly comprises at least one unit (i.e. for example "at least one sensor" or "at least one flow path"), there is thus a limiting case where the assembly comprises a single unit (i.e. for example a single sensor or a single flow path) and the word "each" denotes this single unit.

The calculation means 7 comprise only electronic and/or software technical means (preferably electronic), and comprise a computer central processing unit, and/or a processor, and/or a dedicated analog or digital circuit, and/or software.

The mass flowmeter 4 is a mass flowmeter using thermal conductivity.

Typically, the mass flowmeter 4 comprises a heating element (heat source) and two temperature probes. The heating element is located between the two temperature probes so that the heating element and the two temperature probes are all three aligned in the direction of flow of the gas stream 25 at the mass flowmeter. Depending on the variation of temperature or of quantity of heat between the two temperature probes alongside the heat source, the mass flowmeter 4 is arranged in order to determine the parameter thereof representing the mass flow rate of the gas stream 25 passing through the flowmeter 4 (i.e. a mass of gas passing via the flow path per unit of time).

The advantage of a mass flowmeter, in particular using thermal conductivity, is that it has a very rapid response time. It will therefore enable access to a diameter of leak hole 22 or to a quantification of the presence of a gas of interest with a very high speed of measurement (typical response time of 3 milliseconds).

The at least one flow path comprises:
- a suction path starting at the opening 2 (i.e. the gas stream enters the suction path via the opening 2),
- an exhaust path terminating at the opening 2 (i.e. the gas stream exits the exhaust path via the opening 2), and
- a dilution path terminating at the opening 2 (i.e. the gas stream exits the dilution path via the opening 2).

All these flow paths are possible in the device 1 according to the position of the valve 8 and the direction of the stream 25 generated by the generation means 3. The position of the valve 8 and the direction of the stream 25 generated by the generation means 3 (exhaust or suction) at a given moment determines the single (zero or one selected from the suction path, the exhaust path or the dilution path) flow path through which the gas stream 25 flows at this moment in the device 1.

All the Flow Paths are Closed

For a first position 9 of the valve 8, the valve 8 is closed and the gas stream 25 generated by the means 3 cannot flow along any flow path as defined previously.

Figure 2:
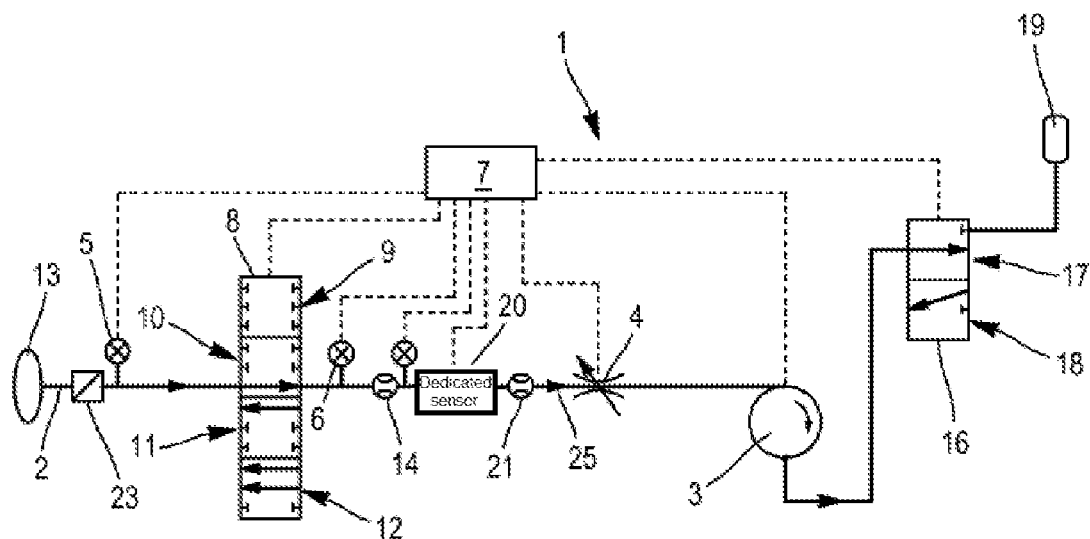
FIG. 2 shows diagrammatically the pneumatic circuit of the device in FIG. 1 in the position for analysing a gas by suction or in the calibration position.
Figure 3:
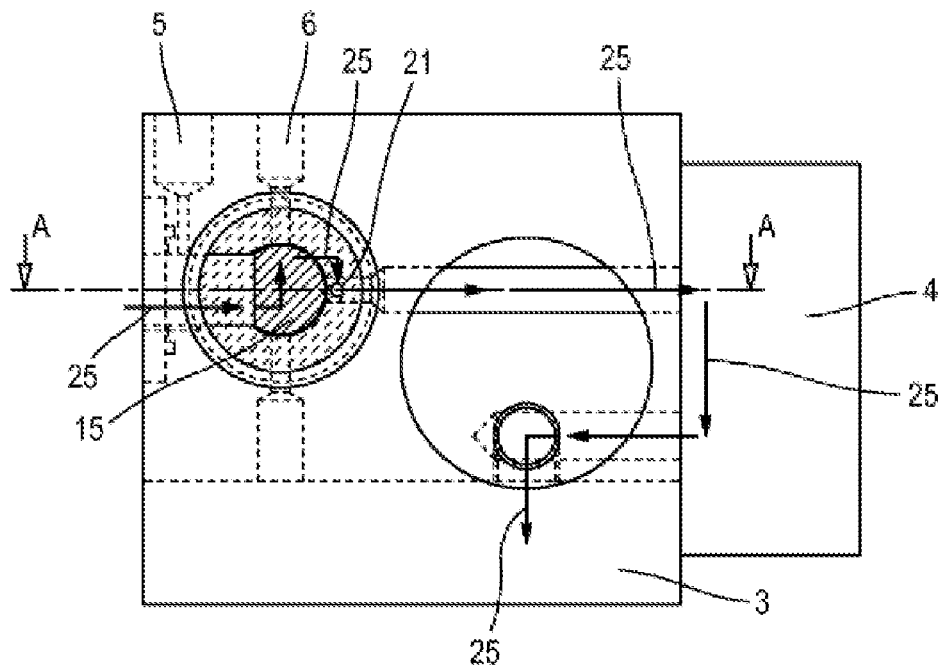
FIG. 3 is a partial diagrammatic cross section view from below of a part of the device in FIG. 1, in which a gas stream is shown when this device is in the position for analysing a gas by suction or in the calibration position.

Suction path With reference to FIGS. 1 to 3, for a second position 10 of the valve 8, and for the generation means 3 sucking in the gas stream 25, the means 3 for generating the gas stream 25 are arranged in order to suck in a gas to be analyzed originating from a sample 13 so that this gas to be analyzed flows into the device 1 along the suction path.

The gas to be analyzed comprises for example:
- 0 to 100% of a mixing gas comprising one or more molecules (for example $N_2$ and $O_2$), each of these molecules having a thermal conductivity differential with the other molecules of the mixing gas of at most 10% (preferably at most 5%) under identical temperature and pressure conditions (typically, for each pair of two molecules of the mixing gas having a thermal conductivity respectively $D_i$ and $D_j$ under identical temperature (temperature of the stream 25 during the pressure measurement $P_r$, typically 20° C.) and pressure conditions (Measurement pressure $P_r$), then $$\frac{D_i - D_j}{D_i} \leq 10\% \text{ and } \frac{D_i - D_j}{Dj} \leq 10\%,$$

or preferably $$\frac{D_i - D_j}{D_i} \leq 5\% \text{ and } \frac{D_i - D_j}{Dj} \leq 5\%);$$

this threshold, which is optimally fixed at 5 or 10% can also be greater than 10% (20%, 30%, etc.) in other embodiments, but the higher this threshold, the worse will be the resolution of the device according to the invention; and 0 to 100% of a gas of interest comprising only one or more molecules (for example $NO_2$ and/or $CO_2$) having between them a thermal conductivity differential less than or equal to 10% (preferably less than or equal to 5%) under identical temperature and pressure conditions (typically, for each pair of two molecules of the gas of interest having a thermal conductivity respectively $C_i$ and under identical temperature (temperature of the stream 25 during the pressure measurement $P_r$, typically 20° C.) and pressure conditions (Measurement pressure $P_r$), then $$\frac{C_i - C_j}{C_i} \leq 10\% \text{ and } \frac{C_i - C_j}{C_j} \leq 10\%,$$

or preferably $$\frac{C_i - C_j}{C_i} \leq 5\% \text{ and } \frac{C_i - C_j}{C_j} \leq 5\%).$$

This threshold which is optimally set at 5 or 10% can also be greater than 10% (20%, 30%, etc.) in other embodiments, but the higher this threshold, the worse will be the resolution of the device according to the invention. Each molecule of the gas of interest has a thermal conductivity different from the thermal conductivity of each of the molecules of the mixing gas of at least 20%, preferably of at least 30%, under identical temperature and pressure conditions (typically, for each molecule of the gas of interest having a thermal conductivity $C_i$ and for each molecule of the mixing gas having a thermal conductivity $D_i$, under identical temperature (temperature of the stream 25 during the pressure measurement $P_r$, typically 20° C.) and pressure conditions (Pressure of measurement $P_r$), then $$\frac{C_i - D_i}{C_i} \geq 20\% \text{ and } \frac{C_i - D_i}{D_i} \geq 20\%,$$

or preferably $$\frac{C_i - D_i}{C_i} \geq 30\% \text{ and } \frac{C_i - D_i}{D_i} \geq 30\%).$$

This difference of at least 20 or 30% affects the accuracy of the device 1; the higher
   it is, the more the gas of interest is differentiated and the use of electronic amplification reduced; this threshold which is optimally set at 20 or 30% can also be less than 20% in other embodiments, but the lower this threshold, the worse will be the resolution of the device according to the invention or the greater will be its need for high-performance electronics for the differentiation, or other redundant technical means of implementation of the device described in other measurement scales.

Within the device 1, said suction path narrows locally at a measurement hole 14. The measurement hole 14 is a hole made in a plate 15. The plate 15 is typically made from stainless steel. The plate 15 is detachable so that it can be replaced typically either in the event of wear of the hole 14 or for changing the size of the hole 14 within the device 1. The hole 14 has a known dimension typically from 5 μm to 150 μm in diameter. The flow passes through a second hole 21 having a greater diameter (typically of the order of 2 mm) than the measurement hole 14. The thickness of this perforated plug 15 is an element for adjusting the sought load drop, and is very much smaller than the size of the microperforated opening 14 (typically approximately 10 times smaller).

This hole 14 is the passage having the smallest aperture area (per unit of surface area perpendicular to the direction of the stream 25) for the gas stream 25 in the device 1 compared with the remainder of the suction path as a whole, and even preferably of the exhaust path and of the dilution path. Typically, all the locations along the suction path (and even preferably the exhaust path and the dilution path), with the exception of the hole 14 itself obviously, have an aperture area (per unit of surface area perpendicular to the direction of the stream 25) at least 5 times greater than the aperture area (per unit of surface area perpendicular to the direction of the stream 25) of the hole 14.

The hole 14 is circular in shape.

The at least one pressure sensor 5, 6 comprises a first pressure sensor 6 (called suction pressure sensor) arranged in order to measure a pressure $P_r$ (more precisely a negative pressure, directly linked to the suction force of the turbine 3) of the gas to be analyzed along the suction path, preferably but non-limitatively comprised between 20 and 500 mbar or wider (comprised between 4 and 500 mbar or comprised between 4 and 1000 mbar or wider according to the capacities of the turbine 3).

The mass flowmeter 4 is arranged in order to measure the parameter representing the mass flow rate of the gas to be analyzed along the suction path.

The calculation means 7 are arranged in order to quantify the presence of a gas of interest within the gas to be analyzed (this quantified presence being typically a proportion in % of gas of interest in the gas to be analyzed or in mol per litre of gas to be analyzed or in the form of a volume of gas of interest for example in millilitres), based on a measurement of the parameter representing the mass flow rate of the gas to be analyzed.

The calculation means 7 are arranged in order to quantify the presence of the gas of interest in the form of a calculation of a proportion or of a volume of the gas of interest which depends on the diameter of the measurement hole 14. In other words, if the diameter or the width of the hole 14 is changed with no indication thereof (by a program, a command, an adjustment knob, etc.) to the device 1, the calculation of the proportion or the volume of the gas of interest by the device 1 becomes inaccurate.

The first suction pressure sensor 6 is situated along the suction path between the opening 2 and the measurement hole 14, for the best measurement accuracy.

The mass flowmeter 4 is situated along the suction path so that the measurement hole 14 is situated along the suction path between the opening 2 and the mass flowmeter 4.

The inventors of the present invention found experimentally that excellent accuracy of measurement of the size of a narrowing hole (for example reference 14 or 22) within a flow could be achieved by passing the gas stream 25 (typically of air) through this hole and by measuring the diameter of this hole $\phi_{cal}$ using the following formula:

$$\phi_{cal} = X\sqrt[4]{\frac{D_m^2}{P_r}} + Y = X\frac{\sqrt[2]{D_m}}{\sqrt[4]{P_r}} + Y$$

(hereinafter referred to as "1st formula")

With $D_m$ the parameter representing the mass flow rate of this gas stream through this hole and $P_r$ the pressure of this gas stream, and X and Y being numerical calibration coefficients.

With respect to the measurement $D_m$, the mass flowmeter 4 is optimized for one or more types of gas having a thermal conductivity default value. For gases having a thermal conductivity differing from this default value, a correction factor is to be applied.

For example, in the case of the Honeywell AWM series mass flowmeter 4, the flow rate $D_m$ measured by this flowmeter 4 must be multiplied by a factor 1 (no correction) if the gas stream is air and/or $N_2$ and/or $O_2$ and/or NO and/or CO and must be corrected by multiplying it by a correction factor $K_{cal}$=1.35 if the gas stream is a stream of $CO_2$ and/or $N_2O$ and/or $NO_2$, or a factor $K_{cal}$=0.5 for He, $K_{cal}$=0.7 for Hz, $K_{cal}$=0.95 for Ar, and $K_{cal}$=1.1 for $CH_4$ and/or $NH_3$, etc. (reference may be made generally to the user instructions for the model of flowmeter 4 used).

Let the gas to be analyzed be assumed to be a mixture of $O_2$ and $CO_2$ originating from the sample 13 and circulating in the device 1 along the suction path; assuming that it is known that these two gases compose the mixture each with a proportion from 0 to 100%, but that the proportions of these two gases are unknown. Reference is made to the case where the actual diameter $\phi_r$ of the hole 14 is 100 μm.

If the calculation means 7 calculate, using the 1st formula previously described, a diameter of the hole 14 $\phi_{cal}$ of 100 μm, the calculation means 7 deduce therefrom either that the proportion of $O_2$ in the mixture is 100%, or that the proportion of $CO_2$ in the mixture is 0%, according to which of these gases is considered to be the gas of interest.

If the calculation means 7 calculate, using the formula for $\phi_{cal}$ previously described, a diameter of the hole 14 of 135 μm, the calculation means 7 deduce therefrom either that the proportion of $O_2$ in the mixture is 0%, or that the proportion of $CO_2$ in the mixture is 100%, according to which of these gases is considered to be the gas of interest.

Generally, if the calculation means 7 calculate, using the formula for $\phi_{cal}$ previously described, a diameter of the hole 14 of $\phi_{cal}$, the calculation means deduce therefrom (using a formula hereinafter called "2nd formula") that the proportion of $CO_2$ in the mixture is $$\frac{\phi_{cal} - \phi_r}{K_{cal} - 1}\%$$

or that the proportion of $O_2$ in the mixture is $$100 - \frac{\phi_{cal} - \phi_r}{K_{cal} - 1}\%$$

according to the gas of interest in question, with Kcal the correction factor of the gas of interest as explained previously (Kcal=1.35 in the case of the $CO_2$).

The calculation means 7 do not have to pass through two steps of calculating the diameter of the hole 14 (1st step, 1st formula) then deducing the proportion of the gas of interest (2nd step, 2nd formula), but can calculate this proportion directly in a single calculation combining both steps and therefore both formulae.

The calculation means 7 are therefore arranged in order to quantify the presence of the gas of interest in the form of a calculation of a proportion or of a volume of the gas of interest which preferably depends affinely on the square root of the parameter $D_m$ representing the mass flow rate.

Optionally, in the less accurate case of a limited development of the first formula to the order one, the calculation means 7 are arranged in order to quantify the presence of the gas of interest in the form of a calculation of a proportion or of a volume of the gas of interest which depends affinely on the parameter representing the mass flow rate.

Generally, in the case of a limited development of the first formula to the order Z (with Z an integer greater than or equal to 1), the calculation means 7 are arranged in order to quantify the presence of the gas of interest in the form of a polynomial of degree Z of the parameter representing the mass flow rate.

In this context it is possible to envisage two variants of the invention that can optionally be combined within a single device 1.

In a first variant, the calculation means 7 are arranged in order to quantify the presence of the gas of interest also from a pressure measurement $P_r$ by the suction pressure sensor:

preferentially, the calculation means 7 are arranged in order to quantify the presence of the gas of interest in the form of a calculation of a proportion or of a volume of the gas of interest which depends affinely on the inverse of the fourth root of the pressure measurement by the suction pressure sensor. The proportion or the volume of the gas of interest is typically calculated according to the formula:

$$A\frac{\sqrt[2]{D_m}}{\sqrt[4]{P_r}} + B$$

with $D_m$ the parameter representing the mass flow rate measured by the flowmeter 4, $P_r$ the pressure measured by the aspiration pressure sensor 6, and A and B being numerical calibration coefficients.

Optionally, approximations may be made. For example, the calculation means 7 can be arranged in order to quantify the presence of the gas of interest in the form of a calculation of a proportion or of a volume of the gas of interest which depends affinely on the inverse of the pressure measurement by the suction pressure sensor 6. The proportion or the volume of the gas of interest is typically calculated according to the formula:

$$M\frac{D_m}{P_r} + N$$

with $D_m$ the parameter representing the mass flow rate measured by the flowmeter 4, $P_r$ the pressure measured by the suction pressure sensor 6, M and N being numerical calibration coefficients.

In a second variant, $P_r$ the pressure measured by the aspiration pressure sensor 6 is not taken into account in the formula for calculating the proportion or the volume of gas of interest, but serves as a trigger: the calculation means 7 are arranged in order to trigger a quantification of the presence of the gas of interest for a value of the pressure $P_r$ measured by the suction pressure sensor 6 corresponding to the suction pressure reference value, the calculation means 7 being arranged in order to quantify the presence of the gas of interest based on a value $D_m$ of the parameter representing the mass flow rate measured simultaneously with the pressure measurement measuring the pressure value corresponding to the suction pressure reference value. The calculation means 7 are then arranged in order to quantify the presence of the gas of interest in the form of a calculation of a proportion or of a volume of the gas of interest:

Preferably according to the formula:

$$A^* \sqrt[2]{D_m} + B$$

will $D_m$ the parameter representing the mass flow rate measurement by the flowmeter 4, and $A^*$ and B being numerical calibration coefficients.

Optionally according to the formula:

$M^* D_m + N$ or any other polynomial of degree Z of $D_m$ as explained previously, with $D_m$ the parameter representing the mass flow rate measured by the flowmeter 4, and $M^*$ and N being numerical calibration coefficients.

According to the invention, all the calibration factors A, B, M, N, $A^*$, $M^*$, a, b, $a^*$ are stored by the calculation means 7 and are defined in advance, typically by calibrating the device 1 with samples 13 with known proportions of different gases or with samples 13 each provided with a leak hole 22 of known dimension.

The value of each calibration factor depends on the gas in question. For example, a mixing gas $O_2$ mixed with a gas of interest $CO_2$ can be assumed, or a mixing gas He mixed with a gas of interest $CH_4 + NH_3$, etc.

The device 1 thus comprises an interface arranged in order to define the mixing gas and the gas of interest, and the calculation means 7 are arranged in order to select the values of the calibration factors depending on the defined mixing gases and gases of interest.

The suction path passes successively through the opening 2, the filter 23, the pressure sensor 5, the valve 8, the pressure sensor 6, the measurement hole 14, the gas sensor 20, the passage hole 21, the flowmeter 4, the generation means 3 and the valve 16.

The device 1 also comprises at least one sensor 20 arranged in order to quantify the presence of a gas constituted by a given molecule the thermal conductivity of which would not be differentiated from that of another gas or molecule present.

The calculation means 7 (for example in a case where the mixing gas is $O_2$ and where the gas of interest is a $CO_2 + NO_2$ mixture) are moreover arranged in order to quantify the presence of a first molecule of interest (for example $CO_2$ in this case) of the gas of interest having a certain thermal conductivity, to this end the device 1 comprising along the suction path at least one gas sensor 20 (for example an $NO_2$ sensor in this case, for example made by City technology) arranged in order to quantify the presence (proportion in % or in mol·l$^{-1}$ or volume for example) of at least one other molecule of interest (for example $NO_2$ in this case) which has a thermal conductivity differing by not more than 10% with respect to the thermal conductivity of the first molecule of interest under identical pressure and temperature conditions, the calculation means 7 being arranged in order to quantify the presence of the first molecule of interest ($CO_2$) based (simple subtraction) on a quantification of the presence of the gas of interest ($CO_2 + NO_2$) and a quantification of the presence of the other molecules of interest ($NO_2$).

For example, if the following are measured:

Proportion of the gas of interest $CO_2 + NO_2 = 20\%$ of the gas to be analyzed Proportion $NO_2 = 5\%$ of the gas to be analyzed Then deducting the following:

Proportion of the mixing gas ($O_2$)=100−Proportion $CO_2 + NO_2 = 80\%$ of the gas to be analyzed Proportion $CO_2 = 15\%$ of the gas to be analyzed The sensor 20 is situated along the suction path so that the measurement hole 14 is situated between the opening 2 and the sensor 20. The sensor 20 is situated in a measurement chamber along the suction path between the measurement hole 14 and a passage hole 21 wider than the measurement hole 14.

The at least one sensor 20 can also be an $O_2$ sensor, or other sensor (for example an $O_2$ sensor and $NO_2$ sensor assembly), for example if the mixing gas comprises a mixture of $O_2$ and $N_2$ this is so as to differentiate these two molecules.

Dilution Path

Figure 4:
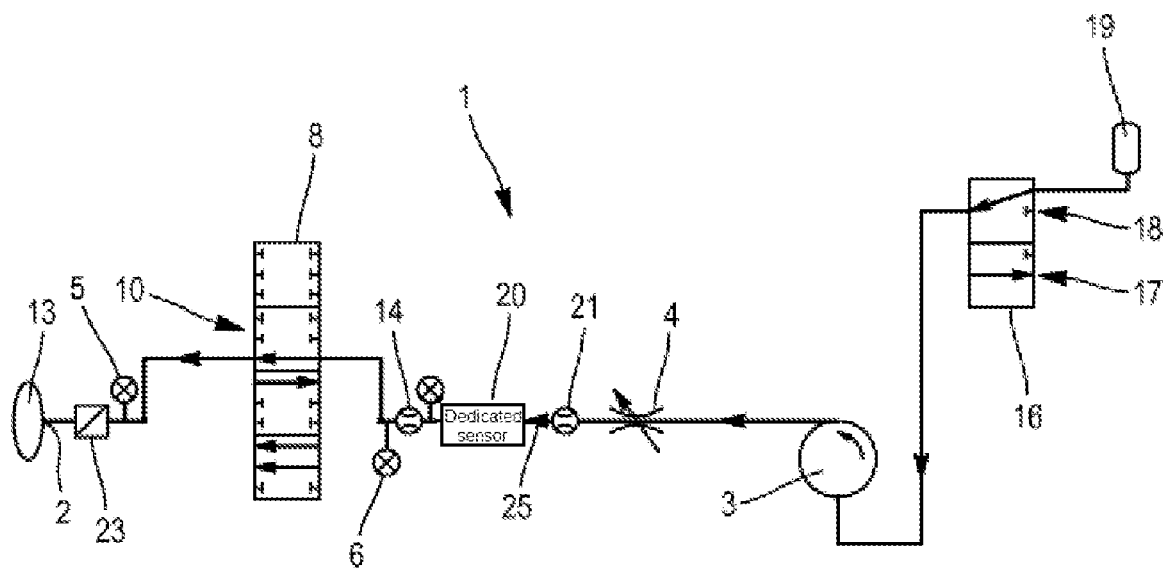
FIG. 4 shows diagrammatically the pneumatic circuit of the device in FIG. 1 in a dilution position or in another calibration position.
Figure 5:
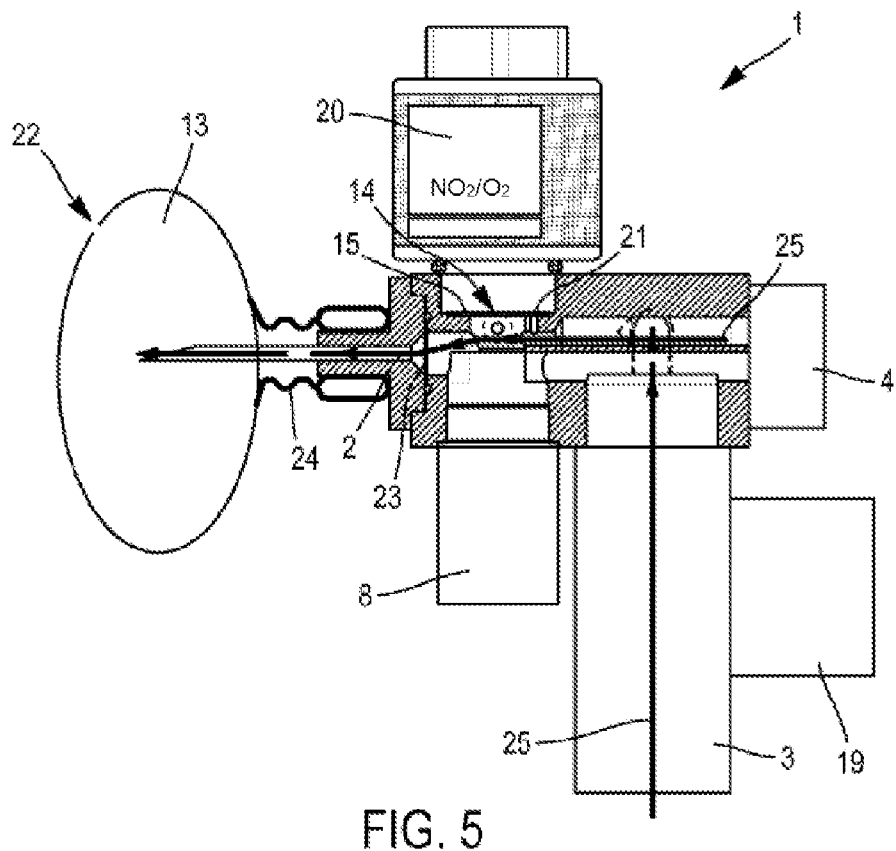
FIG. 5 is a diagrammatic cross section profile view of the device in FIG. 1, showing a gas stream when this device is in a position for detecting a leak by exhaustion.
Figure 6:
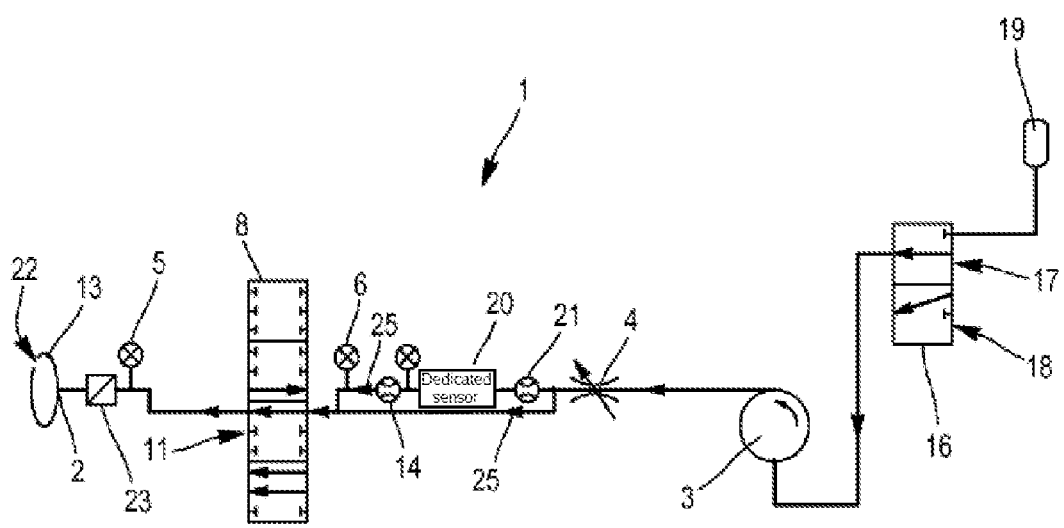
FIG. 6 shows diagrammatically the pneumatic circuit of the device in FIG. 1 in the position for detecting a leak by exhaustion.

With reference to FIG. 4, for the same position (second position 10) of the valve 8 as for the suction path, and for the generation means 3 exhausting the gas stream 25, the means 3 for generating the gas stream 25 are arranged in order to exhaust a dilution gas along the dilution path.

The dilution path therefore corresponds to the suction path but is traveled by the gas stream 25 in the reverse direction.

For the dilution path, the valve 16 is in its second position 18 linking the means 3 to the gas source 19. The solution gas is therefore the reference gas from the source 19 (which is typically a gas cartridge).

The dilution path serves to increase the volume of the gas to be analyzed in the sample 13.

Dilution Path: Example 1

It is assumed that the sample 13 initially only contains as initial gas a mixture of $CO_2 + NO_2$ without $O_2$, but in too small a quantity to be able to suck this mixture into the device 1 filling all of the suction path: it is thus impossible to determine the proportions of $CO_2$ and of $NO_2$ in this case. On the other hand, if $O_2$ originating from the source 19 is introduced into the sample 13 via the dilution path, then the sample 13 contains a mixture of $CO_2 + NO_2 + O_2$ in a quantity sufficient to take measurements. The proportion of $CO_2$, $NO_2$, and $O_2$ can be determined after dilution as described previously. The proportion of $CO_2$ and of $NO_2$ before the dilution can then be deduced therefrom.

For example, if the following are measured:

Proportion $CO_2 + NO_2 = 20\%$ of the gas to be analyzed after dilution

Proportion $NO_2 = 5\%$ of the gas to be analyzed after dilution

Then the following are deduced therefrom:

Proportion $O_2$=100−Proportion $CO_2 + NO_2 = 80\%$ of the gas to be analyzed after dilution Proportion $CO_2 = 15\%$ of the gas to be analyzed after dilution I.e.:

Proportion $NO_2 = 25\%$ of the initial gas before dilution

Proportion $CO_2 = 75\%$ of the initial gas before dilution

Dilution Path: Example 2

It is assumed that sample 13 initially contains only a mixture of $N_2$ and of $O_2$ as initial gas, but in a too small quantity to be able to suck in this mixture in the device 1 filling all of the suction path: it is thus impossible to determine the proportions or volumes of $O_2$ and of $N_2$ in this case. On the other hand, if $CO_2$ originating from the source 19 is introduced into the sample 13 via the dilution path, then the sample 13 contains a mixture of $CO_2+N_2+O_2$ in a quantity sufficient to take measurements. The proportion of $CO_2$, $N_2$, and $O_2$ can be determined after dilution as described previously by using the volume of gas injected and the volume of gas sucked in. The proportion of $CO_2$ and of $N_2$ before the dilution can then be deduced therefrom.

Initial stage: The assumed volume of gas contained is V1 (typically this problem is encountered for sachets the available volume of which is less than 3 ml). This volume V1 is unknown at the initial stage. The volume V1 contains a majority of $N_2$ and traces of $O_2$ that cannot be measured due to the available volume of gas in the container.

Dilution: dilution of the volume is carried out with 100% $CO_2$ by injecting a volume V2=10 ml at least sufficient to excite the $O_2$ sensor (labelled 20).

The volume V2 is then sucked in again.
The proportions given are:
Mixture $O_2+CO_2+N_{2=1.34}$ instead of 1.35 (reference $N_2+O_2$, air)
The quantity of $N_2+O_2$ present in the diluted mixture is = (100−1.34×100/1.35)×V2=0.00296×V2=0.0296 ml
The volume of $CO_2$ contained in V2 is V2−0.037%×V2=9.97 ml
The concentration of $CO_2$ in V2 has become 99.704%
The proportion of $O_2$ in the diluted mixture V2 is given by the sensor 20=0.01%, i.e. 0.001 ml
The proportion of $O_2$ in the initial volume V1 is =0.001×100/0.0296=3.378%
And the volume V1: (100−99.704)*10 ml=2.96 ml can be deduced therefrom Exhaust Path With reference to FIGS. 5 and 6, for a third position 11 of the valve 8, and for the generation means 3 exhausting the gas stream 25, the means 3 for generating the gas stream are arranged in order to exhaust a leakage gas along the exhaust path.

According to the position of the valve 16, the leakage gas (preferably $O_2$ or air) originates from the external atmosphere or from the source 19.

The at least one exhaust pressure sensor comprises an exhaust pressure sensor 5 arranged in order to measure a pressure $P_r$ of the leakage gas along the exhaust path, preferably but non-limitatively comprised between 20 and 500 mbar or wider comprised between 4 and 500 mbar or comprised between 4 and 1000 mbar, and in any case, within the limits of the load drop in the pneumatic circuit and of the pressure resistance of the elements constituting the invention.

The mass flowmeter 4 is arranged in order to measure a parameter representing the mass flow rate of the leakage gas along the exhaust path.

The calculation means 7 are arranged in order to determine the size of a leak hole 22 of the sample 13 (into which is introduced the leakage gas exhausted by the device 1), based on a measurement of the parameter representing the mass flow rate.

The exhaust pressure sensor 5 is situated along the exhaust path between the flowmeter 4 and the opening 2.

The calculation means 7 are arranged in order to determine the size of the leak hole 22 preferably in the form of a calculation which depends affinely on the square root of the parameter representing the mass flow rate (cf. first formula described previously).

Optionally, in the less accurate case of a limited development of the first formula to the first order, the calculation means 7 are arranged in order to determine the size of the leak hole 22 in the form of a calculation which depends affinely on the parameter representing the mass flow rate.

Generally, in the case of a limited development of the first formula to the order Z (with Z an integer greater than or equal to 1), the calculation means 7 are arranged in order to determine the size of the leak hole 22 in the form of a polynomial of degree Z of the parameter representing the mass flow rate.

In this context it is possible to envisage two variants of the invention that can optionally be combined within a single device 1.

In a first variant, the calculation means 7 are arranged in order to determine the size of the hole 22 also based on a measurement of pressure by the exhaust pressure sensor 5, for example in the form of a calculation which depends preferably affinely on the inverse of the fourth root of the pressure measurement. Typically, the calculation means 7 are arranged in order to determine the size of the hole 22 according to the formula:

$$a\frac{\sqrt[2]{D_m}}{\sqrt[4]{P_r}} + b$$

with $D_m$ the parameter representing the mass flow rate measurement by the flowmeter 4, $P_r$ the pressure measured by the exhaust pressure sensor 5, and a and b being numerical calibration coefficients.

According to the invention, it is then possible to measure diameters of leak hole 22 typically up to a minimum of 0.05 µm.

In a second variant, $P_r$ the pressure measured by the exhaust pressure sensor 5 is not taken into account in the formula for calculating the size of the leak hole 22, but serves as a trigger: The calculation means 7 are arranged in order to trigger a determination of the size of the hole 22 for a value of the pressure measured by the exhaust pressure sensor 5 corresponding to an exhaust pressure reference value, the calculation means 7 being arranged in order to determine the size of the hole 22 based on a value of the parameter representing the mass flow rate $D_m$ measured simultaneously with the pressure measurement measuring the pressure value corresponding to the exhaust pressure reference value. The calculation means 7 are for example arranged in order to determine the size of the hole 22 according to the formula:

$$a^* \sqrt[2]{D_m} + b$$

with $D_m$ the parameter representing the mass flow rate measured by the flowmeter 4, and a* and b being numerical calibration coefficients.

The exhaust path divides into two parts which separate before the measurement hole 14 and which rejoin after the measurement hole 14:
- a first part passes through the measurement hole 14, (and comprises the sensor 6 and the measurement chamber comprised between the measurement hole 14 and the passage hole 21)

a second part does not pass through the measurement hole 14, so that the measurement hole 14 does not limit the flow rate of the gas stream 25 exhausted in the exhaust path.

The exhaust path therefore passes successively via the valve 16, the generation means 3, the flowmeter 4, the two parts which divide before the measurement hole 14 and which join after the measurement hole 14, the valve 8, the pressure sensor 5, the filter 23, and the opening 2.

Calibration Path

The at least one flow path comprises a calibration path passing through the opening 2, which corresponds to the suction path or dilution path. This calibration path narrows locally at the measurement hole 14. When the generation means 3 generate a suction or exhaust gas stream 25 (calibration gas) in this calibration path without the opening 2 being connected to a closed sample 13 (the opening 2 preferably opening into the open air), the calculation means 7 are arranged in order to:

1) determine the size of the measurement hole 14 based on a measurement of the parameter representing the mass flow rate $D_m$ by the flowmeter 4, on the same principle as the determination of the size of a leak hole 22 previously described, and
2) adjust its numerical coefficients (typically a, b, a*, etc.) for the calculation of a size of a leak hole 22 if its determination of the size $\phi_{cal}$ of the measurement hole 14 does not correspond to the actual size $\phi_r$ of the measurement hole 14 stored by the calculation means 7,
3) And optionally to reiterate steps 1) and 2) above until the determination of the size of the measurement hole 14 corresponds, with a permitted error percentage, to the actual size of the measurement hole 14 stored by the calculation means.

Short-Circuit Path

Figure 7:
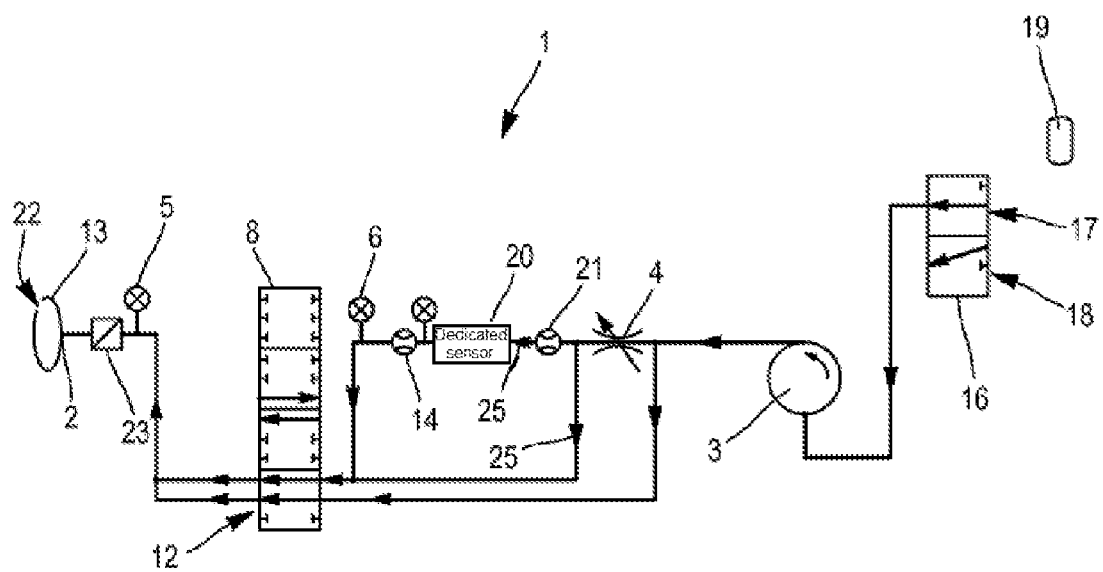
FIG. 7 shows diagrammatically the pneumatic circuit of the device in FIG. 1 in a position of rapid exhaust by inflation.
Figure 8:
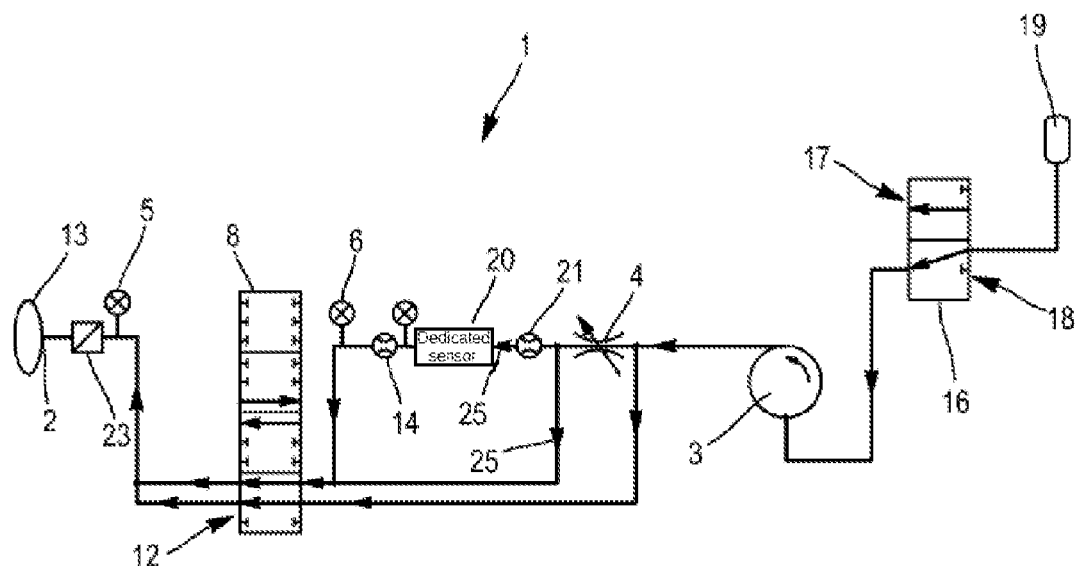
FIG. 8 shows diagrammatically the pneumatic circuit of the device in FIG. 1 in a position of burst by exhaustion.

With reference to FIGS. 7 and 8, the valve 8 in its fourth position 12 is arranged in order to complete the exhaust path via a short-circuit path passing through the opening 2 and the stream generation means 3 but not passing through the flowmeter 4 (this short-circuit path thus not forming part of the flow paths as defined previously). The valve 8 is arranged in order to adjust the total flow rate passing through the exhaust path and the short-circuit path. This allows greater flow rates $D_m$, and thus makes it possible to measure other scales of diameter of the leak hole 22 or to rapidly inflate the sample 13 in order to test its burst strength by successive fatigue or stress phenomena. The calculation means 7 are arranged in order to deduce, based on a flow rate measurement $D_m$ along the exhaust path by the mass flowmeter 4, the total flow rate passing through the exhaust path and the short-circuit path when the valve 8 opens this short-circuit path.

Typically, the calculation means 7 apply a simple multiplication, via a calibration coefficient, of the flow rate $D_m$ measured by the mass flowmeter 4 in order to obtain the total flow rate passing through the exhaust path and the short-circuit path when the valve 8 opens this short-circuit path. Or preferably, the calculation means 7 modify the value of the calibration coefficients a and a* during the determination of the size of the leak hole 22, to take into account the fact that the total flow rate passing through the exhaust path and the short-circuit path is greater than the measurement, by the flowmeter 4, of the parameter $D_m$ representing the mass flow rate of the leakage gas along the exhaust path.

An example will now be described of a process the sequence of which can be modified according to the invention implemented by the device 1 in FIGS. 1 to 8. The types of gas mentioned ($O_2$, $CO_2$, $NO_2$ etc.) are merely for the purposes of illustration and can of course be varied.

Dilution

Firstly, before suction of the gas to be analyzed, the process according to the invention comprises exhausting (via the means 3) of the dilution gas ($CO_2$ originating from the source 19) flowing along the dilution path into the sample 13 comprising an initial gas (mixture of $CO_2$ and $NO_2$) which preferably but not necessarily comprises the gas of interest.

Gas Analysis

After the dilution, the process according to the invention comprises suction (via the means 3) of the gas to be analyzed ($O_2$+$CO_2$+$NO_2$) originating from the sample 13, said sucked gas to be analyzed flowing along the suction path starting at the opening 2 and narrowing locally at the measurement hole 14.

During the suction, the process according to the invention comprises simultaneously:

a measurement of pressure (more precisely a negative pressure of the suction, a priori negative but considered to be an absolute value for the calculations) $P_r$ of the gas to be analyzed along the suction path by the sensor 6, preferably but non-limitatively comprised between −20 and −500 mbar or wider comprised between 4 and 500 mbar or comprised between 4 and 1000 mbar or more according to the capacity of the turbine 3;
a measurement of a parameter representing the mass flow rate of the gas to be analyzed along the suction path, by the flowmeter 4.

The process according to the invention then comprises a quantification, by the calculation means 7, of the presence of the gas of interest ($CO_2$+$NO_2$) within the gas to be analyzed ($O_2$+$CO_2$+$NO_2$), based on this last measurement of the parameter representing the mass flow rate: for example, proportion $CO_2$+$NO_{2=20}$% of the gas to be analyzed after dilution. The quantification of the presence of the gas of interest comprises a calculation as described for the description of the device 1.

The gas of interest ($CO_2$+$NO_2$) comprises from 0 to 100% of a first molecule of interest ($CO_2$) having a certain thermal conductivity, and from 0 to 100% of other molecules of interest ($NO_2$) which have a thermal conductivity differing by at most 10% with respect to the thermal conductivity of the first molecule of interest under identical temperature and pressure conditions.

The process according to the invention also comprises (simultaneously with the measurement of the pressure and of the parameter representing the mass flow rate) a quantification of the presence of the other molecules of interest ($NO_2$) within the gas to be analyzed ($O_2$+$CO_2$+$NO_2$) by means of the sensor 20: for example, proportion $NO_{2=5}$% of the gas to be analyzed after dilution.

The process according to the invention also comprises a quantification of the presence of the first molecule of interest ($CO_2$) in the gas to be analyzed ($O_2$+$CO_2$+$NO_2$) based on the quantification of the presence of the gas of interest ($CO_2$+$NO_2$) within the gas to be analyzed ($O_2$+$CO_2$+$NO_2$) and the quantification of the presence of the other molecules of interest ($NO_2$) within the gas to be analyzed ($O_2$+$CO_2$+ $NO_2$): for example, proportion $CO_{2=15}$% of the gas to be analyzed after dilution.

The process according to the invention also comprises a quantification of the presence of the first molecule of interest ($CO_2$) in the initial gas ($CO_2$+$NO_2$) based on the quantification of the presence of the first molecule of interest ($CO_2$)

within the gas to be analyzed ($O_2+CO_2+NO_2$) and the quantification of the presence of the other molecules of interest ($NO_2$) within the gas to be analyzed ($O_2+CO_2+NO_2$): for example, proportion $CO_{2=75}\%$ of the initial gas.

The process according to the invention also comprises a quantification of the presence of the other molecules of interest ($NO_2$) in the initial gas ($CO_2+NO_2$) based on the quantification of the presence of the first molecule of interest ($CO_2$) within the gas to be analyzed ($O_2+CO_2+NO_2$) and the quantification of the presence of the other molecules of interest ($NO_2$) within the gas to be analyzed ($O_2+CO_2+NO_2$): for example, proportion $NO_{2=25}\%$ of the initial gas.

Then, the mechanical test of the sample 13 takes place.

Calibration of the Leak Measurement

The process according to the invention then comprises a flow (generated via the means 3) of a calibration gas (preferably external air or the gas from the source 19) along the calibration path and, simultaneously with this flow:
1) a pressure measurement $P_r$ of the calibration gas along the calibration path by the sensor 5 or 6, preferably but non-limitatively comprised between 20 and 500 mbar or wider comprised between 4 and 500 mbar or comprised between 4 and 1000 mbar
2) a measurement of a parameter representing the mass flow rate of the calibration gas along the calibration path, by the flowmeter 4
3) a determination of the size of the measurement hole 14 based on this last measurement of the parameter representing the mass flow rate, by the calculation means 7, and
4) an adjustment, by the calculation means 7, of calibration coefficients a, a*, b for the calculation of a size of a leak hole 22 if the determination $\phi_{cal}$ of the size of the measurement hole 14 does not correspond to an actual size $\phi_r$ of the measurement hole 14 stored by the calculation means, and
5) optionally a reiteration of the preceding steps 1 to 4.

Leak Measurement

The process according to the invention then comprises exhausting the leakage gas (preferably external air or the gas from the source 19 or a tracer gas making it possible to locate the leak, which is a colorant or can be measured by other external means) flowing along the exhaust path terminating at the opening 2.

During the exhausting, the process according to the invention comprises simultaneously:
- a measurement of pressure $P_r$ of the leakage gas along the exhaust path by the sensor 5, preferably but non-limitatively comprised between 20 and 500 mbar or wider comprised between 4 and 500 mbar or comprised between 4 and 1000 mbar, and in any case, within the limits of the load drop in the pneumatic circuit and of the pressure resistance of the elements constituting the invention.
- a measurement of a parameter representing the mass flow rate of the leakage gas along the exhaust path, by the flowmeter 4.

The process according to the invention then comprises a determination, by the calculation means 7, of the size of the leak hole 22 in the sample 13, based on this last measurement of the parameter representing the mass flow rate.

The determination of the size of the leak hole 22 comprises a calculation as described for the description of the device 1.

If the leak hole 22 is too large, the flow rate of the leakage gas must be increased in order to seek to achieve a set-point pressure. The process according to the invention then comprises an adjustment, by the valve 8 arranged in order to complete the exhaust path via a short-circuit path passing through the opening and the stream generation means but not passing through the flowmeter, of the total flow rate passing through the exhaust path and the short-circuit path, said valve opening the short-circuit path according to an opening of adjustable size.

The process according to the invention then comprises a determination, by the means 7, and based on the measurement of flow rate along the exhaust path, of the total flow rate passing through the exhaust path and the short-circuit path when the valve opens the short-circuit path.

More specifically, the calculation means 7 modify the value of the calibration coefficients a and a* during the determination of the size of the leak hole 22, in order to take into account the fact that the total flow rate passing through the exhaust path and the short-circuit path is greater than the measurement, by the flowmeter 4, of the parameter $D_m$ representing the mass flow rate of the leakage gas along the exhaust path.

Strength/Burst Test

After determination of the size of the leak hole 22, the gas flow rate is raised to a high value, optionally at a controlled flow rate in order to burst-test the sample 13 with desired dynamics.

It is noted that in a process according to the invention, the sample 13 can be subjected to extreme mechanical stresses such as a restrictive overwrap, atmospheric pressure, immersion in a fluid, etc.

It is also noted that the different steps of this process can be reversed, or carried out simultaneously or be optional. For example, the calibration step is not necessary before the leak measurement. Similarly, the leak measurement is completely independent of the gas analysis, and the leak measurement can be carried out before the gas analysis or without the gas analysis. In a preferential case, in order to save time, the leak measurement can be carried out simultaneously with the dilution, preferably once an equilibrium pressure has been reached, the exhausted dilution gas also acting as exhausted leakage gas.

Of course, the invention is not limited to the examples which have just been described, and numerous adjustments can be made to these examples without exceeding the scope of the invention.

Of course, the different features, forms, variants and embodiments of the invention can be combined with each other in various combinations insofar as they are not incompatible or mutually exclusive. In particular, all the variants and embodiments described previously can be combined together.

The invention claimed is:

1. A device for testing a sample via a gas stream, comprising:
   an opening arranged to be linked to the sample, the sample being a closed enclosure,
   a reference gas source that is distinct from external air;
   a flow generator configured for generating a gas stream in the device along at least one flow path passing through the opening,
   at least one pressure sensor, each pressure sensor configured to measure a pressure of the gas stream along at least one flow path, and
   a thermal mass flowmeter configured to use thermal conductivity to measure a parameter representing the mass flow rate of the gas stream along each flow path,
   the at least one flow path comprises an exhaust path originating from the reference gas source and terminating at the opening that is linked to the sample, the flow generator generating the gas stream configured to exhaust a leakage gas along the exhaust path, the at least one pressure sensor comprises an exhaust pressure sensor configured to measure a pressure of the leakage gas along the exhaust path, the thermal mass flowmeter configured to measure a parameter representing the mass flow rate of the leakage gas along the exhaust path, and calculation means configured to determine a dimension of a leak hole in a surface of the closed enclosure, based on a measurement of the parameter representing the mass flow rate along the exhaust path, wherein the calculation means determine the dimension of the leak hole based on the measurement:
   from the thermal mass flowmeter configured to use thermal conductivity, and
   measured on the reference gas exhausted from the reference gas source and having a given thermal conductivity.

2. The device according to claim 1, further comprising an exhaust pressure sensor situated along the exhaust path between the flowmeter and the opening.

3. The device according to claim 1, wherein the calculation means are configured to determine the dimension of the leak hole in the form of a calculation which depends linearly on the square root of the parameter representing the mass flow rate along the exhaust path.

4. The device according to claim 1, wherein the calculation means are configured to determine the dimension of the leak hole also based on a measurement of the pressure along the exhaust path by the exhaust pressure sensor.

5. The device according to claim 4, wherein the calculation means are configured to determine the dimension of the leak hole in the form of a calculation which depends linearly on the inverse of the fourth root of the measurement of the pressure along the exhaust path.

6. The device according to claim 5, wherein the calculation means are configured to determine the size dimension of the leak hole according to the formula $$a \frac{\sqrt[2]{D_m}}{\sqrt[4]{P_r}} + b$$

with $D_m$ the parameter representing the mass flow rate, $P_r$ the pressure measured by the exhaust pressure sensor, and a and b being numerical calibration coefficients.

7. The device according to claim 1, wherein the calculation means are configured to trigger a determination of the dimension of the leak hole for a value of the pressure along the exhaust path measured by the exhaust pressure sensor corresponding to an exhaust pressure reference value, the calculation means being arranged to determine the dimension of the leak hole based on a value of the parameter representing the mass flow rate along the exhaust path measured simultaneously with the pressure measurement measuring the pressure value corresponding to the exhaust pressure reference value.

8. The device according to claim 7, wherein the calculation means are configured to determine the dimension of the leak hole according to the formula $$a^* \sqrt[2]{D_m} + b$$

with $D_m$ the parameter representing the mass flow rate, and $a^*$ and b being numerical calibration coefficients.

9. The device according to claim 1, wherein the at least one flow path comprises a calibration path passing through the opening, and in that within the device, said calibration path narrows locally at a measurement hole, the calculation means being configured to:
   determine a dimension of the measurement hole based on a measurement of the parameter representing the mass flow rate along the calibration path, and
   adjust calibration coefficients for the calculation of the dimension of a leak hole if the determination of the dimension of the measurement hole does not correspond to an actual size of the measurement hole stored by the calculation means.

10. The device according to claim 1, further comprising a valve configured to complete the exhaust path via a short-circuit path passing through the opening and the flow generator but not passing through the flowmeter, said valve being arranged to adjust the total flow rate passing through the exhaust path and the short-circuit path.

11. The device according to claim 1, wherein the reference gas source is a gas cartridge.

12. A process for testing a sample via a gas stream, the process comprising:
   exhausting a reference gas of a reference gas source as a leakage gas along an exhaust path originating from the reference gas source and terminating at an opening linked to the sample, wherein the sample is a closed enclosure and the reference gas is distinct from external air;
   measuring the pressure of the leakage gas along the exhaust path,
   measuring a parameter representing the mass flow rate of the leakage gas along the exhaust path, wherein the measuring of the parameter representing the mass flow rate is a measurement by a thermal mass flowmeter using thermal conductivity, and
   determining a dimension of a leak hole in a surface of the closed enclosure, based on the measurement of the parameter representing the mass flow rate along the exhaust path from the thermal mass flowmeter configured to use thermal conductivity, and measured on the reference gas exhausted from the reference gas source and having a given thermal conductivity.

13. The process according to claim 12, wherein the pressure measurement is carried out by an exhaust pressure sensor situated along the exhaust path between the flowmeter and the sample.

14. The process according to claim 12, wherein the determination of the dimension of the leak hole comprises a calculation of the dimension of the leak hole which depends linearly on the square root of the parameter representing the mass flow rate along the exhaust path.

15. The process according to claim 12, wherein the determination of the dimension of the leak hole is carried out also based on the pressure measured along the exhaust path.

16. The process according to claim 15, wherein the determination of the dimension of the leak hole comprises a calculation of the dimension of the leak hole which depends linearly on the inverse of the fourth root of the measurement of the pressure along the exhaust path.

17. The process according to claim 16, wherein the determination of the dimension of the leak hole comprises a calculation of the dimension of the leak hole according to the formula $$a\frac{\sqrt[2]{D_m}}{\sqrt[4]{P_r}}+b$$

with $D_m$ the parameter representing the mass flow rate, $P_r$ the pressure measured, and a and b being numerical calibration coefficients.

18. The process according to claim 12, wherein the determination of the dimension of the leak hole is triggered in the case of a measured value of the pressure along the exhaust path corresponding to a pressure reference value, the determination of the dimension of the leak hole being carried out based on a value of the parameter representing the mass flow rate along the exhaust path measured simultaneously with the pressure measurement measuring the pressure value corresponding to the pressure reference value.

19. The process according to claim 18, wherein the determination of the dimension of the leak hole comprises a calculation of the dimension of the leak hole according to the formula $$a^*\sqrt[2]{D_m}+b$$

with $D_m$ the parameter representing the mass flow rate, and a* and b being numerical calibration coefficients.

20. The process according to claim 12, wherein the at least one flow path comprises a calibration path passing through the opening and narrowing locally at a measurement hole, wherein the process includes:
- a calibration gas flowing along the calibration path,
- a pressure measurement of the calibration gas along the calibration path,
- a measurement of a parameter representing the mass flow rate of the calibration gas along the calibration path,
- a determination of a dimension of the measurement hole based on a measurement of the parameter representing the mass flow rate, and
- an adjustment of numerical coefficients for the calculation of the dimension of a leak hole if the determination of the dimension of the measurement hole does not correspond to an actual size of the measurement hole stored by calculation means.

21. The process according to claim 20, further comprising an adjustment, by a valve configured to complete the exhaust path via a short-circuit path passing through the opening and the stream generation means but not passing through the flowmeter, of the total flow rate passing through the exhaust path and the short-circuit path.

22. The process according to claim 12, wherein the reference gas source is a gas cartridge.

* * * * *